(12) United States Patent
Santaniello et al.

(10) Patent No.: US 11,234,853 B2
(45) Date of Patent: Feb. 1, 2022

(54) THORACIC LUMBAR SACRAL ORTHOSIS BACK BRACE

(71) Applicant: ORTHOCARE MEDICAL EQUIPMENT, LLC, Manchester, NH (US)

(72) Inventors: Steve Santaniello, Milford, NH (US); Rita Carney, Auburn, NH (US)

(73) Assignee: ORTHOCARE MEDICAL EQUIPMENT, LLC, Manchester, NH (US)

(*) Notice: Subject to any disclaimer, the term of this patent is extended or adjusted under 35 U.S.C. 154(b) by 224 days.

(21) Appl. No.: 16/788,407

(22) Filed: Feb. 12, 2020

(65) Prior Publication Data
US 2020/0268543 A1 Aug. 27, 2020

Related U.S. Application Data

(60) Provisional application No. 62/810,598, filed on Feb. 26, 2019.

(51) Int. Cl.
*A61F 5/02* (2006.01)

(52) U.S. Cl.
CPC .............. *A61F 5/028* (2013.01); *A61F 5/02* (2013.01)

(58) Field of Classification Search
CPC .... A61F 5/00; A61F 5/02; A61F 5/024; A61F 5/028; A61F 5/32; A61F 5/34; A61F 5/026; A61F 5/24; A61F 5/26; A61F 5/28; A41D 13/0007; A41D 13/0525; A41D 13/0531; A41D 13/0562; A41D 13/0518; A41D 13/0568; A41D 13/055; A41D 13/0587; A41D 2400/48; A41F 15/00; A41F 15/02; A41F 15/002; A41F 9/00; A41F 9/02; A41F 9/005; A41F 11/00; A41C 1/00; A41C 1/08; A45F 3/04; A45F 3/005; A45F 3/14; A45F 2003/045; A45F 2003/142; A45F 19/00; A61B 17/00; A61B 17/0057

USPC ........ 602/5, 19, 20; 128/846, 869, 870, 871, 128/875, 876

See application file for complete search history.

(56) References Cited

U.S. PATENT DOCUMENTS

| | | |
|---|---|---|
| 2,808,050 A | 10/1957 | Ward |
| 3,094,984 A | 6/1963 | Jewett |
| 3,945,376 A | 3/1976 | Kuehnegger |
| 5,449,338 A | 9/1995 | Trudell |
| 6,063,047 A | 5/2000 | Minne |
| 6,790,191 B1 | 9/2004 | Hendricks |
| 7,967,767 B2 | 6/2011 | Ogilvie |
| 8,308,670 B2 | 11/2012 | Sandifer et al. |
| 8,556,840 B2 | 10/2013 | Burke et al. |
| 9,095,418 B2 | 8/2015 | Cardinali et al. |
| 2010/0318010 A1* | 12/2010 | Sandifer ............. A61F 5/026 602/19 |

(Continued)

*Primary Examiner* — Alireza Nia
*Assistant Examiner* — Daniel A Miller
(74) *Attorney, Agent, or Firm* — KPIP Law, PLLC; Kimberly A. Peaslee

(57) ABSTRACT

The system and method of an adjustable thoracic lumbar sacral orthosis back brace. The brace has a bowtie portion and a three point adjustment system. The bowtie is resistant to twisting due to internal reinforcement. The brace prevents trunk rotation and "hiking up" of the brace during adjustment by a wearer. The bowtie portion resists twisting of a thoracic panel via a channel formed by fixation to a thoracic stabilizer.

11 Claims, 7 Drawing Sheets

(56) References Cited

U.S. PATENT DOCUMENTS

| | | | |
|---|---|---|---|
| 2014/0018715 A1* | 1/2014 | Ingimundarson | A61F 5/026 |
| | | | 602/19 |
| 2015/0133843 A1* | 5/2015 | Turrini | A61F 5/026 |
| | | | 602/19 |
| 2018/0116856 A1 | 5/2018 | Ingimundarson et al. | |
| 2018/0303699 A1 | 10/2018 | Romo et al. | |
| 2019/0046345 A1* | 2/2019 | Garth | A61F 5/028 |

* cited by examiner

THORACIC LUMBAR SACRAL ORTHOSIS BACK BRACE

CROSS-REFERENCE TO RELATED APPLICATIONS

This application claims the benefit of U.S. Provisional Patent Application 62/810,598, filed Feb. 26, 2019, entitled "THORACIC LUMBAR SACRAL ORTHOSIS BACK BRACE," the content of which is incorporated by reference herein in its entirety.

FIELD OF THE DISCLOSURE

The present disclosure relates to orthotic braces and more particularly to a thoracic lumbar sacral full back orthoses.

BACKGROUND OF THE DISCLOSURE

There are many forms of orthoses, or devices used externally to modify the structure and/or function of the skeletal and/or neuromuscular systems of the body. For example, there are orthoses that are applied to the neck, to the spine, to the upper limbs, and to the lower limbs. Additionally, there are many different purposes for using orthoses ranging from rehabilitative to prophylactic. Rehabilitative braces are typically used to limit the movement of a portion of the body following an injury or a surgery.

Orthoses can be used for many purposes. Orthoses can restrict movement in one or more directions, immobilize an area of the body, assist movement of a particular joint or region of the body, reduce the forces applied to an area of the body, aid rehabilitation by preventing reinjury, correct the motion of a portion of the body to reduce pain or improve function.

Conventional back braces contain a lumbar portion that is secured around a user's waist. Conventional full back braces include a rigid panel that is coincident with a wearer's spine. The top of the rigid panel is connected to a pair of shoulder straps that connects back to the lumbar portion. These braces typically "ride up" when the shoulder straps are adjusted to fit the particular wearer.

Conventional full back braces also tend to allow excess trunk rotation for the wearer, which can set recovery back or even reinjure the wearer. In addition to "riding up" and permitting excess trunk rotation, conventional full back braces tend to twist out of alignment when a wearer is donning the brace. It is understood that for an injured person the act of adjusting and donning the brace should be a simple as possible and not require another user to help align the brace properly for the particular application.

In U.S. Pat. No. 6,063,047 a minimal brace comprising a single back panel and single anterior panel is shown. This brace does not offer a universal fit (must purchase sized) and has minimal adjustment for vertical sizing (per size only 2 vertical slots). The brace furthermore cannot be reconfigured. The strap configuration of the brace extends down from the wearer's shoulders and loops into the middle of the back panel and out to the anterior panel. At the point of connection near the middle of the back panel the brace loops directly into slots in the panel.

In U.S. Pat. No. 8,308,670, tightening straps are directly connected to the back-panel frame and continue to connect directly to the distal portion of the same back panel frame. This configuration, when downward pressure is applied, creates a "hike up" phenomenon by the user. Tightening of the straps, in turn, then forces the brace upwards and allows the lumbar compression system to slide up out of alignment to the lower spine.

Wherefore it is an object of the present disclosure to overcome the above-mentioned shortcomings and drawbacks associated with conventional full back braces.

SUMMARY OF THE DISCLOSURE

One aspect of the present disclosure is a system comprising a thoracic lumbar sacral orthosis back brace, comprising: a lumbar portion, comprising: a central portion; and a pair of belts, adjustably connected to the central portion; a thoracic portion, comprising: a central thoracic portion; a thoracic panel; and a pair of shoulder straps being connected at a first end of the thoracic panel; a bowtie portion of fixed length being fixedly attached to a central thoracic stabilizer to form a channel for slidably engaging with a second end of the thoracic panel; and a pair of adjustment straps forming a three point adjustment system such that a first pair of adjustment points is located at free ends of the pair of shoulder straps, a second pair of attachment point is located at each of a pair of fixed loops attached to respective end regions of the bowtie portion, and the third pair of attachment points comprise a pair of connection points each located on one of the adjustable belts.

These aspects of the disclosure are not meant to be exclusive and other features, aspects, and advantages of the present disclosure will be readily apparent to those of ordinary skill in the art when read in conjunction with the following description, appended claims, and accompanying drawings.

BRIEF DESCRIPTION OF THE DRAWINGS

The foregoing and other objects, features, and advantages of the disclosure will be apparent from the following description of particular embodiments of the disclosure, as illustrated in the accompanying drawings in which like reference characters refer to the same parts throughout the different views. The drawings are not necessarily to scale, emphasis instead being placed upon illustrating the principles of the disclosure.

DETAILED DESCRIPTION OF THE DISCLOSURE

Certain lumbar and sacral orthoses are used to partially or fully immobilize the trunk (or torso) of a wearer for a number of purposes including protection after surgery or injury as well as prophylactically to prevent injury or reinjury during activities that typically cause back injuries. Orthoses are also used to protect a wide variety of structures, not just the vertebrae, including intervertebral discs, nerves, the spinal cord, ligaments, muscles, and the like. When worn during the acute stage, post-surgical or post-injury, a brace is typically worn whenever the patient is upright and/or ambulatory (e.g., when out of bed) to protect and stabilize the surgical/injury site. When worn prophylactically, a brace is typically only worn during specific activities to prevent deterioration of the trunk musculature. Braces can vary in height, which can determine the amount of immobilization provided. In certain embodiments, this variation in height will control sagittal plane motion or flexion and extension of the spine. In certain embodiments, a shorter brace limits motion in the lumbar and upper sacral region, while a taller brace limits motion in the lower thoracic, lumbar, and upper sacral vertebrae. In certain embodiments, extensions can be added to control coronal plane motion or side-bending.

Another use of orthoses, as described herein, is in spinal unloading. This application is based on the premise that increasing intra-abdominal pressure results in decreased compressive forces. This is achieved using anterior and posterior panels along with a rigid belt to deliver a compressive force to the abdominal cavity. When the belt is tightened, compressive forces are applied to the trunk of the patient.

There are numerous indications for spinal bracing as described herein, including, but not limited to, acute and chronic strains or sprains in the torso area, postural correction, spinal unloading, degenerative disc disease, post-surgical fusion, laminectomy or discectomy, congenital or traumatic instability, herniated disc(s), spinal stenosis, fractures, spondylolisthesis, spondylolysis, spondylosis, and facet syndrome.

It is understood, that in an effort to maximize the benefits of an orthopedic brace it must be properly fitted and adjusted to the patient. Adjustment variables include fitting patients of various sizes and body proportions, and accommodating a variety of possible surgical or injury sites. The adjustment of the brace will also be continual as the patient heals and can tolerate larger ranges of motion, as swelling is reduced, and the like.

Figure 1A:
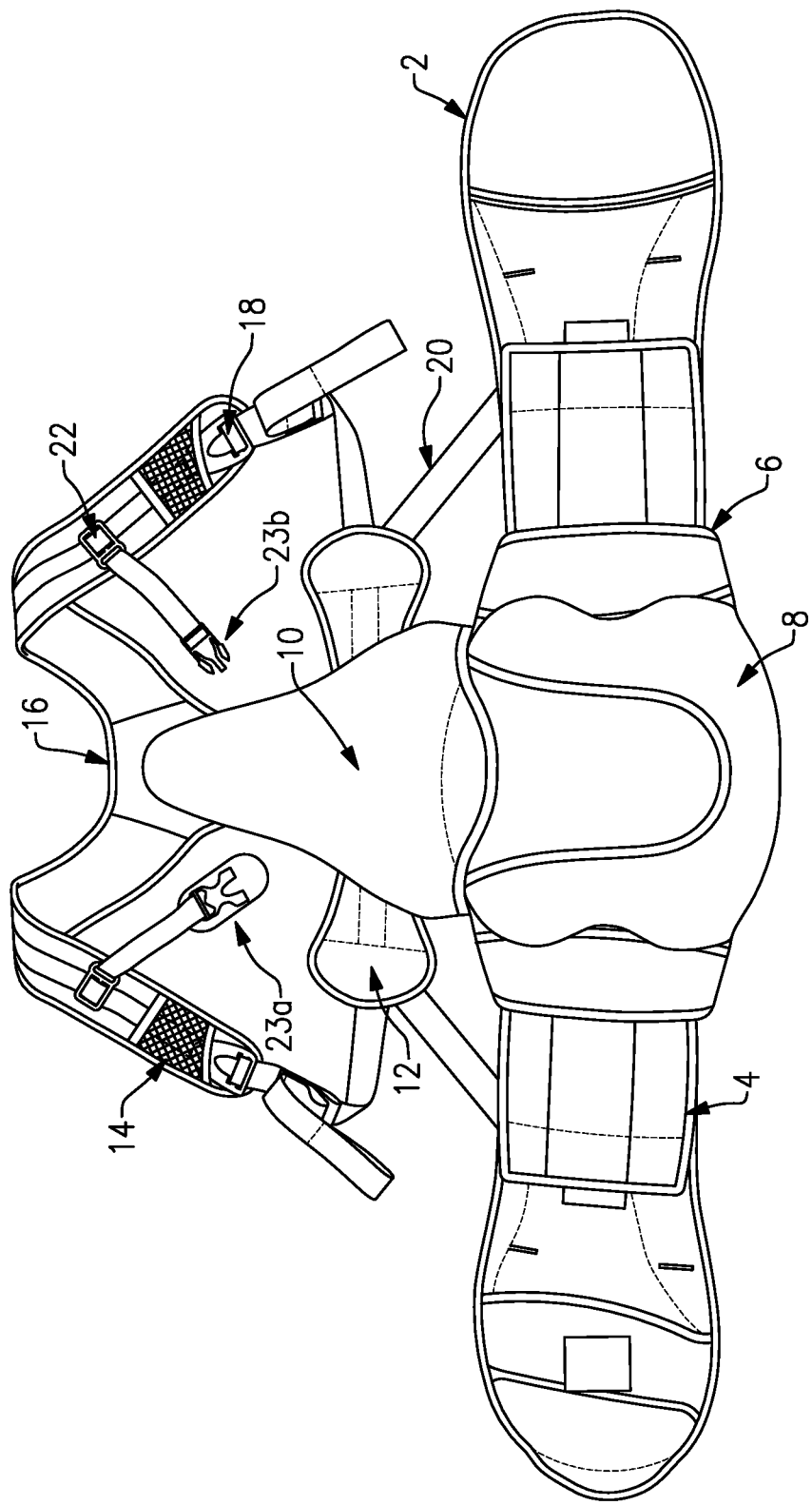
FIG. 1A shows the interior face of one embodiment of the back brace of the present disclosure.

Referring to FIG. 1A, a view of the interior face of one embodiment of the back brace of the present disclosure is shown. More specifically, one embodiment of a lumbar portion 2 comprises a pair of removable belts 4 that connect with a central panel 6. The central lumbar panel has a fixed width. The use of a pair of adjustable belts 4 connected to the central panel 6 provides for a range of sizes possible from a single brace. In some embodiments, the central lumbar panel 6 has additional removable lumbar pads 8 depending on the particular application.

Still referring to FIG. 1A, a central thoracic portion 10 extends up from the central lumbar panel 6. A bowtie portion 12 having a fixed length is woven through the central thoracic portion 10 and is oriented parallel to the lumbar portion 2. The bowtie portion has a first end and a second end extending beyond the central thoracic portion such that the bowtie portion has a length that is the same as the width of the central panel 6. A pair of shoulder straps 14 is fixed to a height adjustable thoracic panel 16, which inserts into the central thoracic portion 10. Each of the shoulder straps 14 has a quick release buckle 18 that attaches to one of a pair of adjustment straps 20. In some embodiments, the full back brace has a sternum strap 22 for reversibly joining the two shoulder straps 14 at the front torso of the wearer via buckles 23a, 23b or other appropriate fasteners.

Figure 1B:
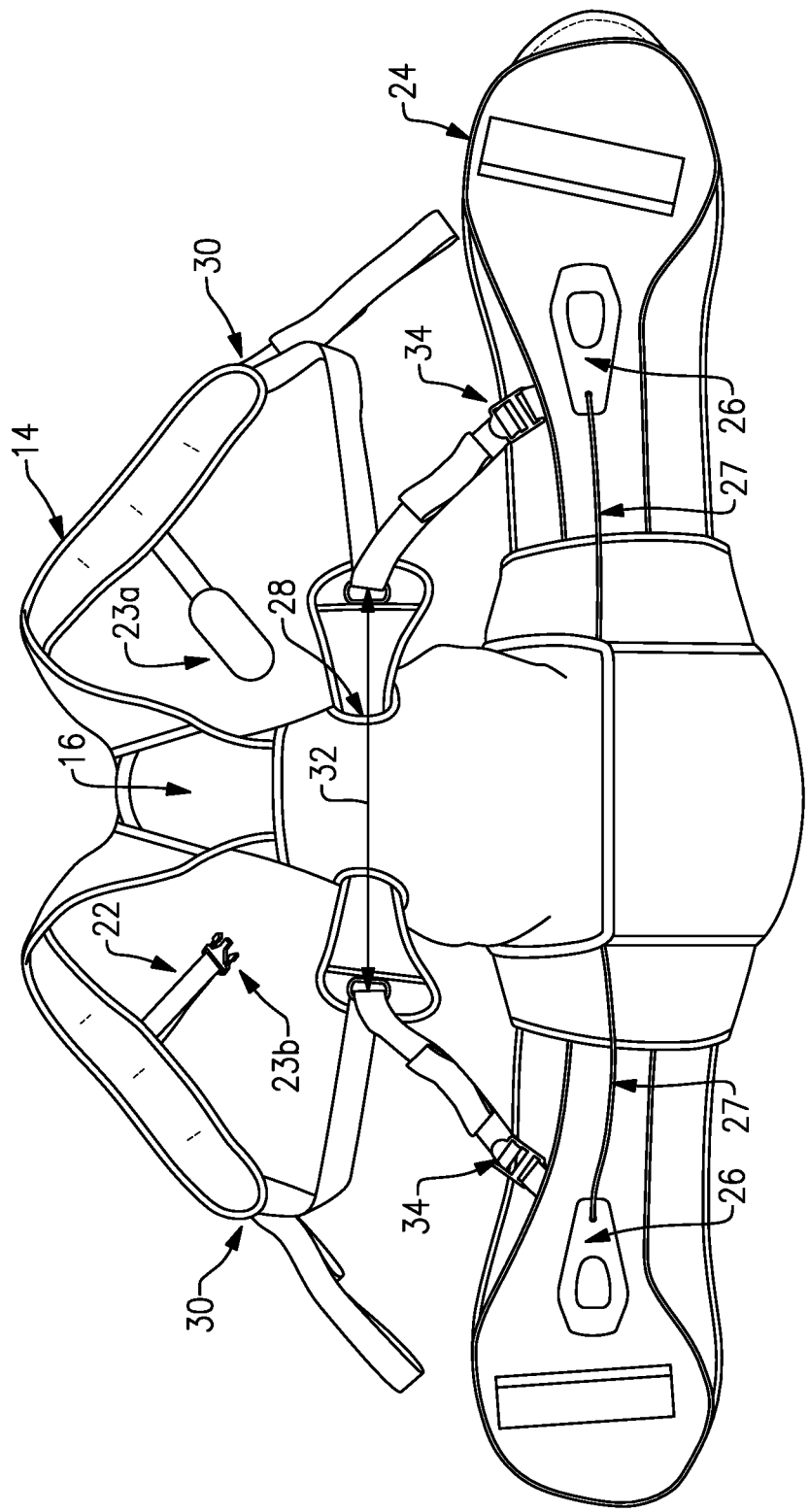
FIG. 1B shows the exterior face of one embodiment of the back brace of the present disclosure.

Referring to FIG. 1B, a view of the exterior face of one embodiment of the back brace of the present disclosure is shown. More specifically, one embodiment of the lumbar portion 2 comprises a pair of finger loops 24 for use in donning and adjusting the lumbar portion and a pair of pull tabs 26 that connect with the central panel to provide fine adjustment of the lumbar portion once the lumbar portion is donned by the wearer.

Still referring to FIG. 1B, the thoracic panel 16 extends up from and out of the central thoracic portion 10. The bowtie portion is woven through a pair of holes 28 in the central thoracic portion and the bowtie portion is oriented parallel to the length of the lumbar portion defined by the pair of belts. A pair of shoulder straps 14 is flexibly fixed to the height adjustable thoracic panel 16. Each of the shoulder straps 14 attaches to an adjustment strap 20 at a first connection point 30. In certain embodiments, the first connection point provides for adjusting the length of the adjustment strap as well as a quick release buckle for ease of removing the brace. A second connection point 32 is located on the bowtie portion and is used for routing the adjustment strap. A third connection point 34 is located on the lumbar portion and is at the other end of the adjustment strap. The third connection point also provides for adjusting the length of the adjustment strap to properly fit the brace to a wearer. Each of the connection points (30, 32, and 34) on either side of the brace are in contact with the same adjustment strap 20 providing for three points of contact for the brace. In some embodiments, the full back brace also has a sternum strap 22 for reversibly joining the two shoulder straps at the front torso of the wearer.

Figure 2B:
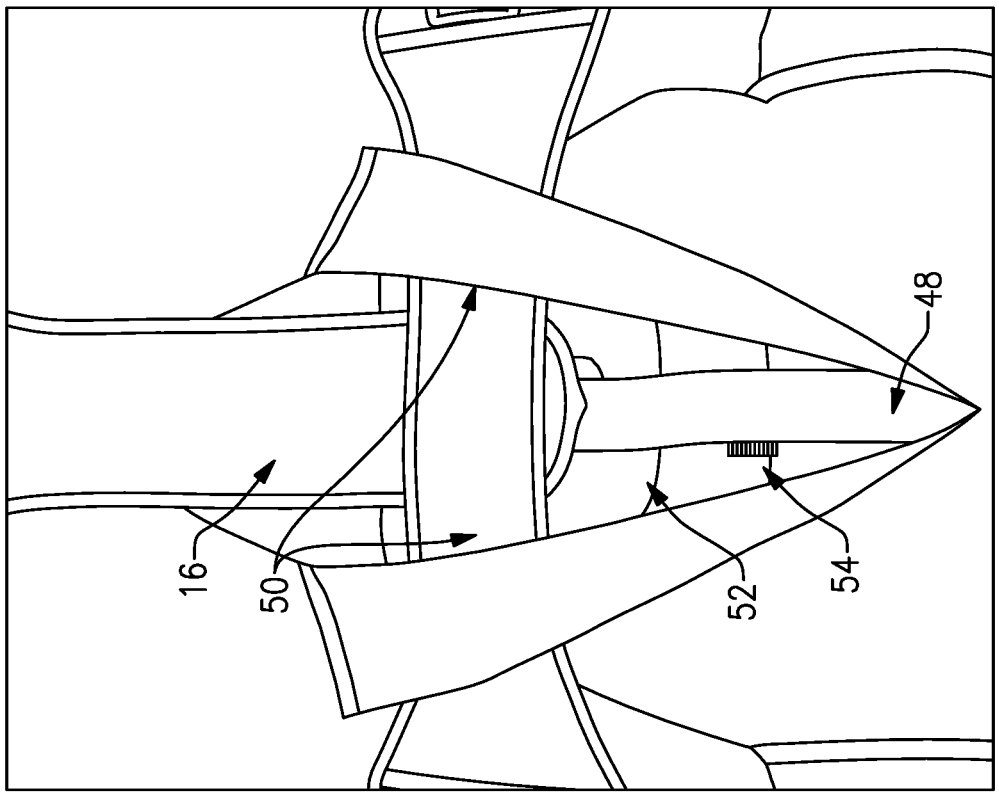
FIG. 2B shows another view of a portion of the exterior face of one embodiment of the back brace of the present disclosure with the adjustable thoracic panel being removed to show how the brace is constructed.
Figure 2A:
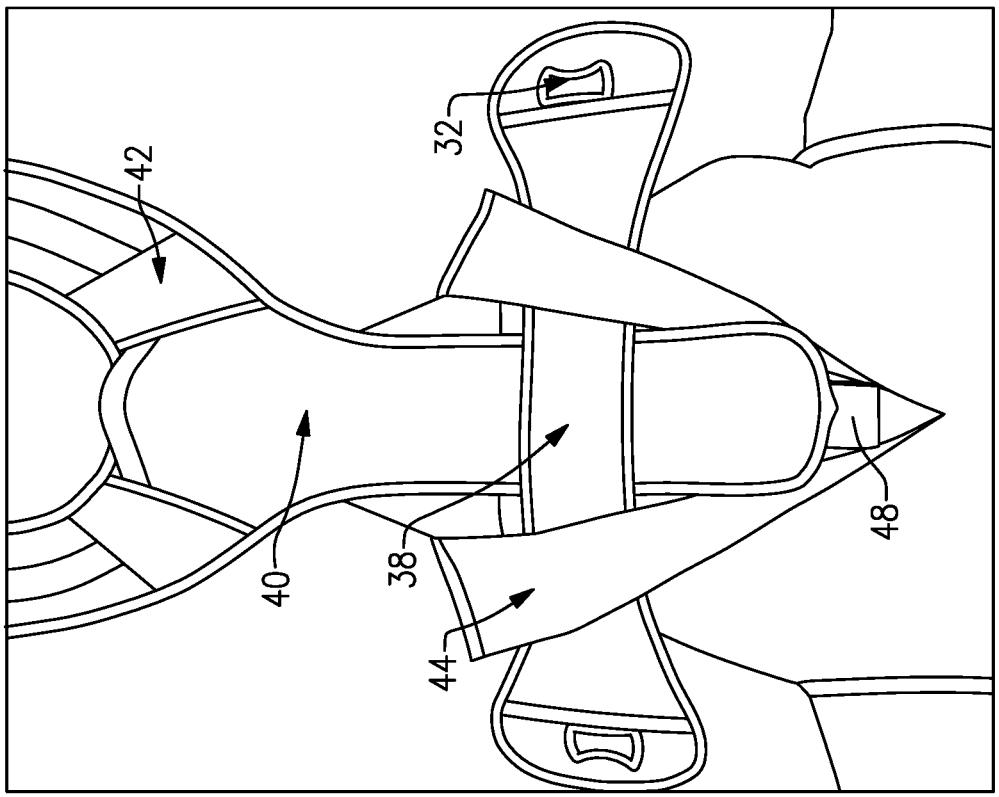
FIG. 2A shows a view of a portion of the exterior face of one embodiment of the back brace of the present disclosure to show how the brace is constructed.

Referring to FIG. 2A, a view of a portion of the exterior face of one embodiment of the back brace of the present disclosure to show how the brace is constructed is shown. More specifically, an exterior layer 44 has been cut away to reveal the internal structural relationship between the bowtie 38 and the height adjustable thoracic panel 16. Inside the height adjustable thoracic panel 16 is a stabilizer 40 that is separate from a pair of arm strap stabilizers 42, the stabilizers are visible though the mesh like fabric in this embodiment. In certain embodiments, the stabilizer for the thoracic panel comprises high density polyethylene (HDPE) sheet or laminated HDPE. In some cases, the stabilizer for the thoracic panel is present as series of layers including HDPE sheet to foam. In some cases the arm strap stabilizers are made of a different material than the stabilizer for the thoracic panel. In some cases, the arm strap stabilizers comprise layers of quilted fabric and cross-linked foam inserts for cushioning.

Still referring to FIG. 2A, the exterior layer 44 may comprise nylon. In some cases, the exterior layer is also present on the outer facing surface of the bowtie portion when the brace is donned by a wearer. At the base of the height adjustable thoracic panel, is a connector 48. In some cases it is a strap. In certain embodiments, the connector further comprises hook and loop. A pair of loops 32 are fixed to the bowtie portion, such that they are a fixed distance apart from each other and each equidistant from a centerline of the height adjustable thoracic panel that is coincident with a longitudinal axis of the height adjustable thoracic panel.

Referring to FIG. 2B, another view of a portion of the exterior face of one embodiment of the back brace of the present disclosure with the adjustable thoracic panel being removed to show how the brace is constructed is shown. More specifically, the height adjustable thoracic panel 16 is shown with the connector 48 detached from the lumbar portion of the brace so that the lumbar portion can be separated from the height adjustable thoracic panel. In this view, it is possible to see that the bowtie portion is fixedly attached 50 to a central thoracic stabilizer 52 to provide a "channel" for accepting the height adjustable thoracic panel 16. This channel provides for extra stability and also mitigates any twisting of the height adjustable thoracic panel 16 when installed. In some embodiments, the bowtie portion is sewn to the central thoracic stabilizer 52. In some cases, the central thoracic stabilizer comprises LDPE plastic, or the like. In this view, an area of the upper back panel 54 is also shown. This will be described in more detail in at least FIG. 2D.

Figure 2D:
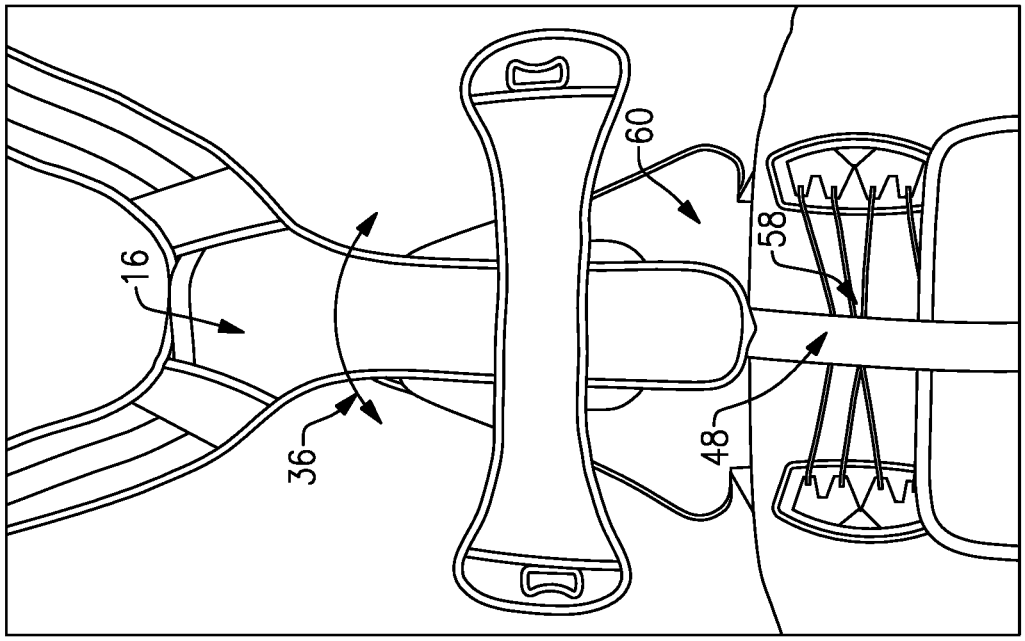
FIG. 2D shows a view of a portion of one embodiment of the back brace of the present disclosure with an outer layer removed to show how the brace is constructed.
Figure 2C:
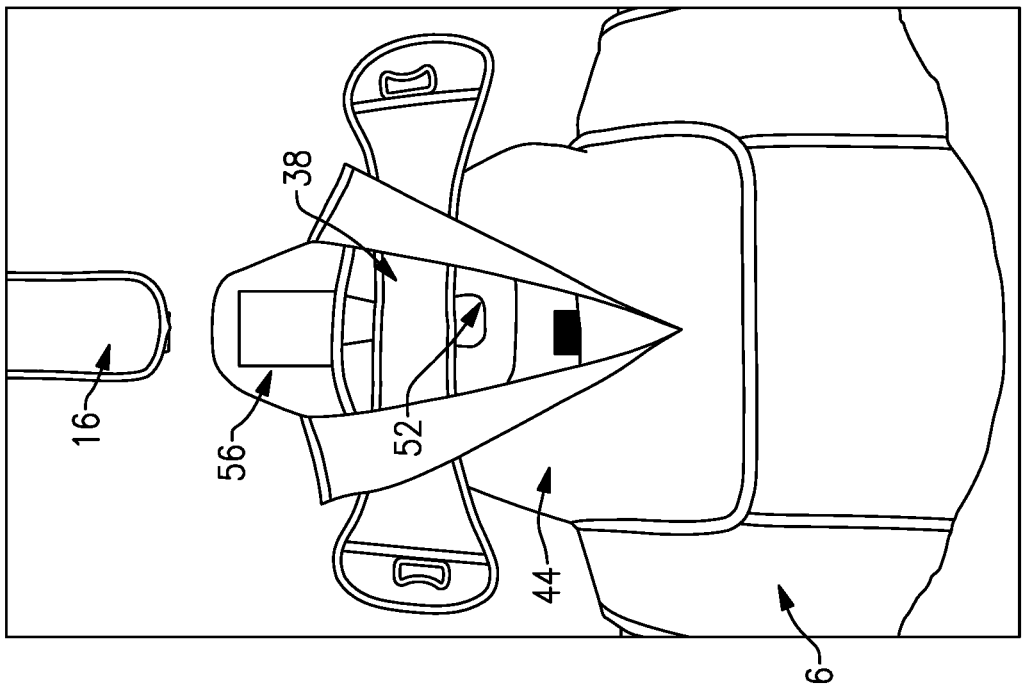
FIG. 2C shows another view of a portion of the exterior face of one embodiment of the back brace of the present disclosure with the adjustable thoracic panel being further removed to show how the brace is constructed.

Referring to FIG. 2C, another view of a portion of the exterior face of one embodiment of the back brace of the present disclosure with the height adjustable thoracic panel being further removed is shown. More specifically, the height adjustable thoracic panel 16 (with the connecter not visible) has been separated from the central lumbar panel 6. The bowtie 38 is shown fixedly connected to the central thoracic stabilizer 52 which is covered by an exterior layer 44 through which the bowtie 38 is woven and having a pocket 56 for accepting the central thoracic stabilizer 52.

Referring to FIG. 2D, a view of a portion of one embodiment of the back brace of the present disclosure with the outer layer removed to show how the brace is constructed is shown. More specifically, the upper portion of the back panel 60 is shown. In this embodiment is approximately triangular shape and its base is broader adjacent the central back panel area. The connector 48 is shown unattached to the harness cord 58 of the lumbar portion. When connected, the connector 48 is looped around the harness cord 58 to hold the adjustable height thoracic panel 16 at a desired height to better fit a particular wearer. As noted previously, a central thoracic stabilizer is fixedly attached to the bowtie portion to create a channel for accepting and for holding the adjustable height thoracic panel in an orientation that is perpendicular to the bowtie. The structural design of the present disclosure prevents, at the least, the twisting of the brace along an arc 36 to restrict unwanted movement within the frontal or coronal plane of the wearer. Due, in part to the connectivity and construction of the present brace when donned by a wearer, movement within the sagittal plane of the wearer (equivalent to in and out of the plane of the page) is also restricted.

Figure 3B:
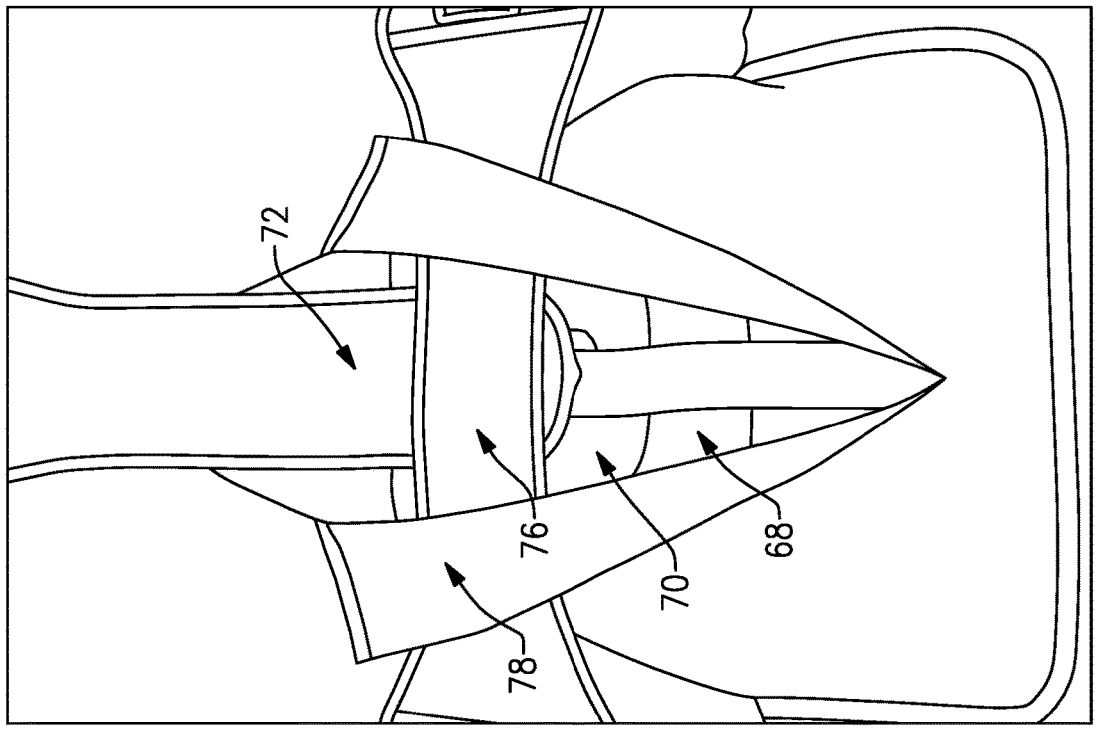
FIG. 3B shows a view of a portion of the exterior face of one embodiment of the back brace of the present disclosure to show the plurality of layers.
Figure 3A:
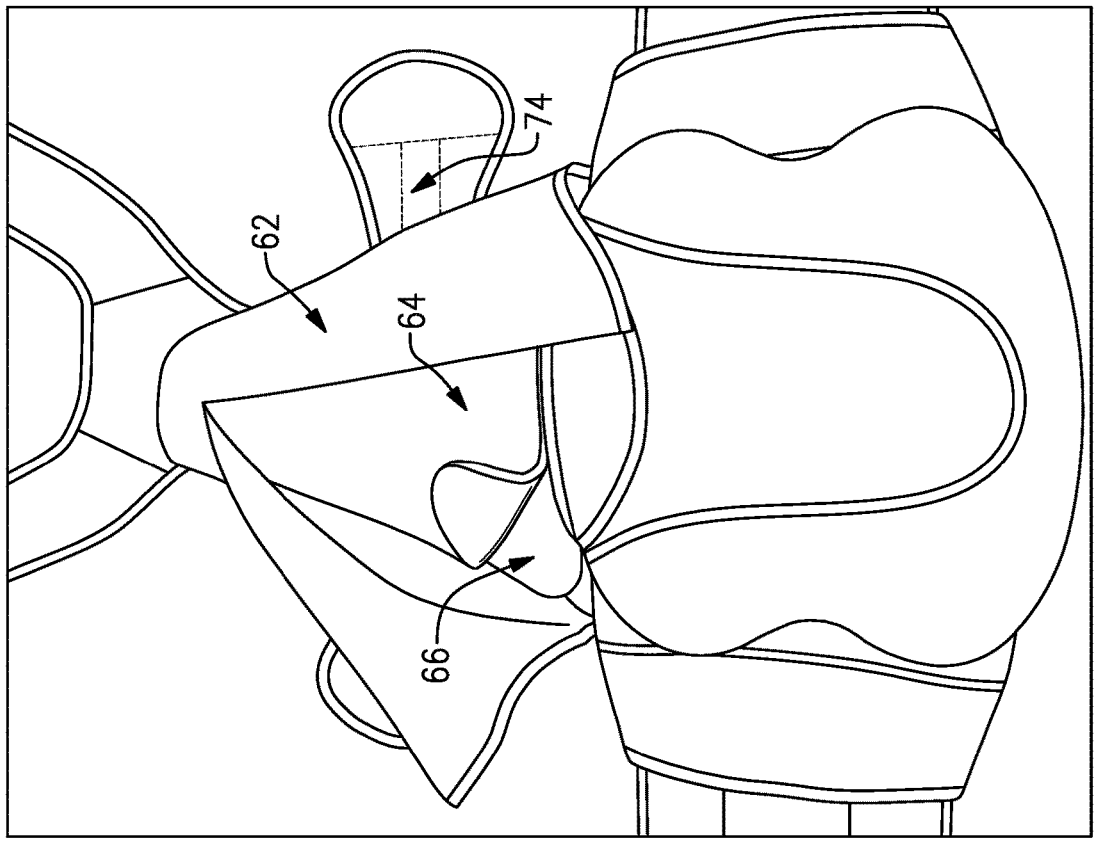
FIG. 3A shows a view of a portion of the interior face of one embodiment of the back brace of the present disclosure to show the plurality of layers.

Referring to FIG. 3A, a view of a portion of the interior face of one embodiment of the back brace of the present disclosure is shown to highlight the plurality of layers. More specifically, an innermost layer 62 (in reference to when the brace is donned by a wearer) comprises phase change materials (PCM) that absorb, store, and release heat for optimal thermal comfort. In certain embodiments the PCM is encapsulated in a polymer shell and gives the brace the ability to continually regulate the wearer's skin's temperature to maximize comfort. The next layer (progressing from the wearer out) is a foam layer 64, where the foam layer is followed by a plastic layer 66. In one embodiment, the plastic is ABS (acrylonitrile butadiene styrene) or other thermoplastic with impact resistance. In certain embodiments, the foam layer is attached to the plastic player, e.g. using adhesive. The innermost layer 62 may be referred to as an interior layer. The next layer 64 may be referred to as a first intermediate layer. The plastic layer 66 may be referred to as a second intermediate layer.

Referring to FIG. 3B, a view of a portion of the exterior face of one embodiment of the back brace of the present disclosure to show the plurality of layers is shown. More specifically, still progressing from the wearer out, the next layer is the upper portion of the back panel 68. In some cases, this panel comprises a rigid, heat moldable plastic. In some cases, the upper portion of the back panel 68 is a cross linked polyurethane foam pad applied to the back of the plastic layer 66 (shown in FIG. 3A).

Still referring to FIG. 3B, the central thoracic stabilizer 70 is formed to match the top portion of the upper portion of the back panel 68 and to fit into the pocket formed by the outer layer. In some embodiments, the central thoracic stabilizer 70 has one or more recesses in the central region. The central thoracic stabilizer 70 is fastened to the bowtie portion 76 to form a channel through which the thoracic panel 72 can slide. The thoracic panel 72 is sandwiched between the inner surface of the bowtie portion 74 and the central thoracic stabilizer 70. In some embodiments, the inner surface of the bowtie portion 74 comprises PCM and the outer surface of the bowtie portion (facing away from the wearer) is made of a synthetic fabric (e.g., nylon). In some cases, the external layer 78 is comprised of the same material as the external surface of the bowtie portion.

Figure 4A:
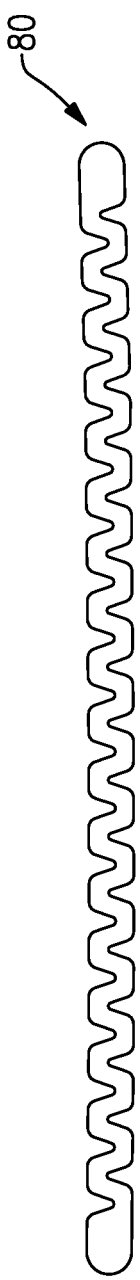
FIG. 4A shows one embodiment of a stay for one embodiment of a bowtie portion of a back brace of the present disclosure.
Figure 4B:
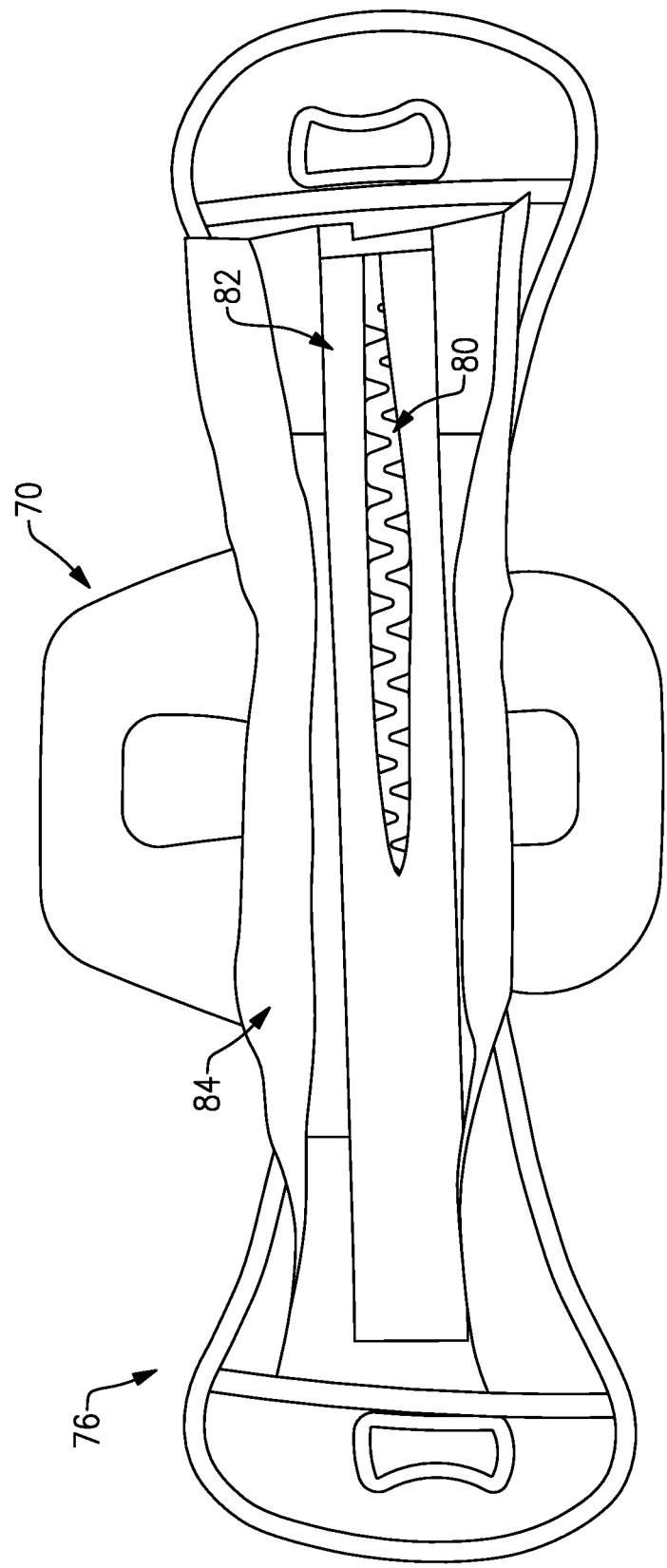
FIG. 4B shows one embodiment of a bowtie portion of a back brace of the present disclosure.

Referring to FIG. 4B, one embodiment of a bowtie portion of a back brace of the present disclosure is shown. More specifically, one embodiment of the central thoracic stabilizer 70 is shown fixed to the bowtie portion 76. A stay 80, such as is shown in FIG. 4A, is used to provide additional rigidity to the bowtie portion. In some cases the stay comprises plastic. In some embodiments, the stay extends a portion of the total length of the bowtie portion. In some cases, a zig-zag stay is chosen because it allows for multi-directional flexibility. The material is generally a form of plastic.

Still referring to FIG. 4B, in certain embodiments, the stay 80 is surrounded by a strap 82 and the strap is embedded into the interior of the bowtie portion as defined as being within the one or more exterior layers 84. The bowtie, once assembled, is sewn or otherwise fixed to the central thoracic stabilizer 70 along both sides of the central thoracic stabilizer 70 to create a channel through which the thoracic panel can slide up and down to provide for a variety of overall effective heights for the lumbar brace of the present disclosure.

The thoracic lumbar sacral orthosis back brace of the present disclosure is designed to be fitted to individual wearers. In one embodiment, the back panel of the brace is preset at 5° lordosis and can be adjusted further by a professional using a heat gun. Once the back panel has been adjusted to a wearer the overall length of the lumbar portion is adjusted by adjusting the belt lengths. In certain embodiments, the belt lengths are adjusted via hook and loop attachments and are based on the circumference of the waist of a wearer. In addition to adjusting the back panel and the belt lengths, there is a need to adjust the shoulder harness height using the thoracic panel. The wearer is measured from the base of the neck (e.g., C7) to the top of the sacrum to determine the overall height of the thoracic lumbar sacral orthosis back brace of the present disclosure. The connector is separated from the harness cord and the thoracic panel is slid up or down within the channel formed by the bowtie and the central thoracic stabilizer to a desired height. Once the height is achieved, the connector is secured to the harness. In some cases, the thoracic panel is secured to the harness via a hook and loop closure.

Prior to the wearer donning the brace of the present disclosure the brace is prepared. In some cases, the pull tabs are set equidistant form the central lumbar portion. The shoulder straps are loosened and then the brace is slid onto the wearer's shoulders like a back pack. The thoracic panel is centered on the wearer's back and the wearer inserts their hands into the finger loops and pulls the ends of the belts ways from each other to ensure the lumbar portion is fully lengthened. The wearer then wraps the belt around their waist. To further tighten the lumbar portion, the pull tabs are used for fine adjustment. In certain embodiments, an optional sternum strap is used. This strap provides additional comfort to the wearer by pulling the shoulder straps away from the axilla.

Figure 5:
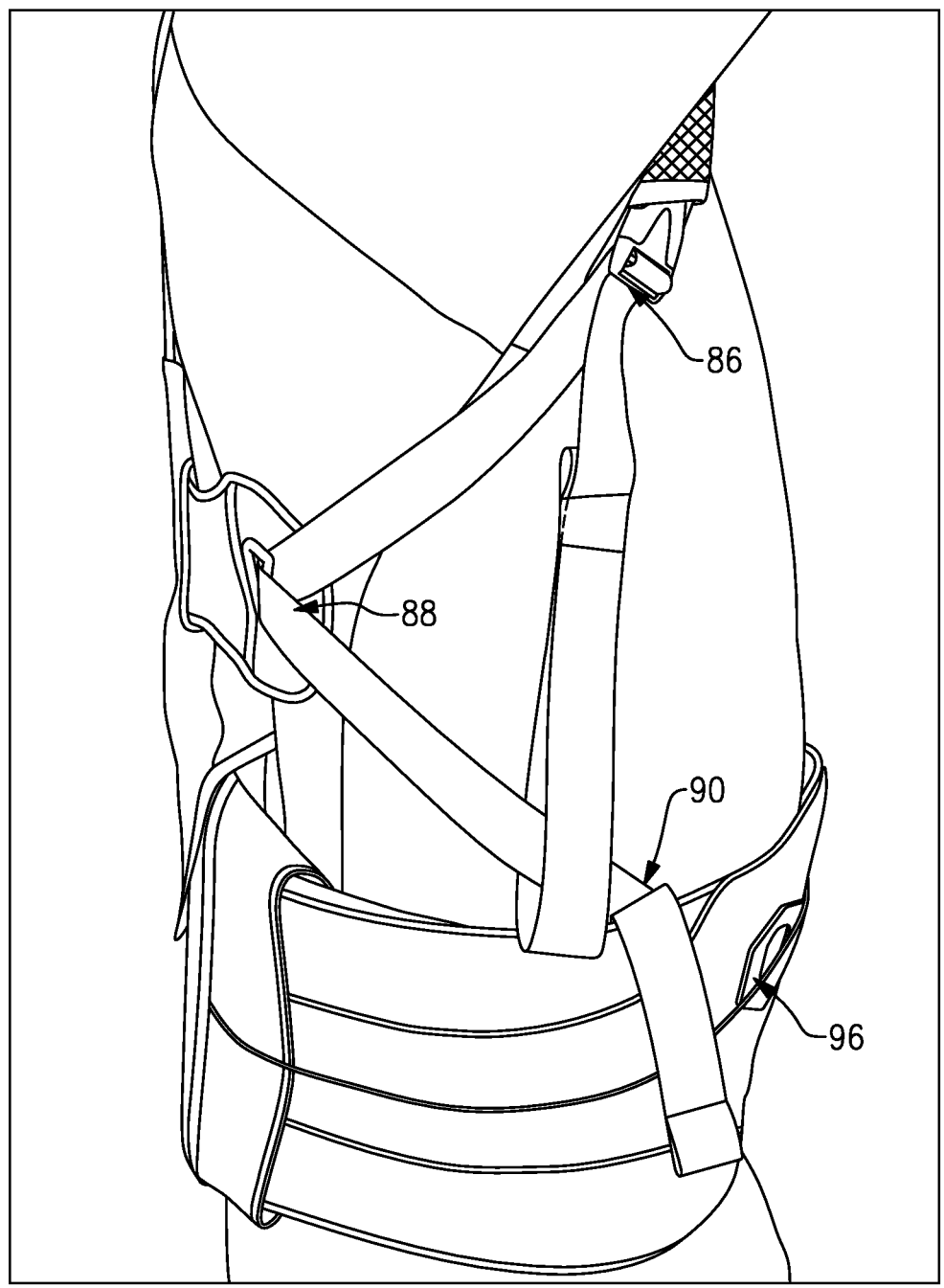
FIG. 5 shows one embodiment of the three point adjustment system of the present disclosure.

Referring to FIG. 5, one embodiment of the thoracic lumbar sacral orthosis back brace of the present disclosure has a three point adjustment system. More specifically, the shoulder straps are tightened via the first adjustment point 86. In certain embodiments, the first adjustment point can be tightened and loosened by the wearer. The second adjustment point 88 is constructed via the adjustment straps as they pass through the fixed loops on the end regions of the bowtie portion. The third adjustment point 90 is defined by the connection point located on each belt portion of the lumbar portion of the back brace. In certain embodiments, the connection point can be tightened and loosened by the wearer.

The design of the present thoracic lumbar sacral orthosis back brace of the present disclosure prevents "hiking up" of the lumbar portion of the brace when the brace is adjusted via the three point adjustment mechanism. Trunk rotation is reduced via the use of the bowtie portion. The bowtie portion provides for fixed placement of the second adjustment point near the midline of the wearer. The bowtie portion further prevents twisting for the thoracic panel and twisting of the bowtie portion itself via an internal stabilizer, e.g., a stay.

The present brace has a total of 7" vertical adjustment for the extension of the upper thoracic support and is a modular system with the ability to remove or replace multiple panels. Additionally, the straps of the brace of the present disclosure never attach directly to the back panel. The flexible horizontal "bowtie" support and its unique layered method offer a unified system and create the leverage of the three-point system. The brace of the present disclosure offers a secure back panel connected to the lower lumbar pulley system of the brace. The torso "wings" are secured through a hinge that is independent of the back panel and pulley system. When the straps are pulled by the user the force travels through the "bowtie" system down to the "wings" and creates a unified compressive force without "hiking up" the panel. Wherefore it is an object of the present disclosure to overcome the above-mentioned shortcomings and drawbacks associated with conventional full back braces While various embodiments of the present invention have been described in detail, it is apparent that various modifications and alterations of those embodiments will occur to and be readily apparent to those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having," and variations thereof herein, is meant to encompass the items listed thereafter and equivalents thereof as well as additional items while only the terms "consisting of" and "consisting only of" are to be construed in a limitative sense.

The foregoing description of the embodiments of the present disclosure has been presented for the purposes of illustration and description. It is not intended to be exhaustive or to limit the present disclosure to the precise form disclosed. Many modifications and variations are possible in light of this disclosure. It is intended that the scope of the present disclosure be limited not by this detailed description, but rather by the claims appended hereto.

A number of implementations have been described. Nevertheless, it will be understood that various modifications may be made without departing from the scope of the disclosure. Although operations are depicted in the drawings in a particular order, this should not be understood as requiring that such operations be performed in the particular order shown or in sequential order, or that all illustrated operations be performed, to achieve desirable results.

While the principles of the disclosure have been described herein, it is to be understood by those skilled in the art that this description is made only by way of example and not as a limitation as to the scope of the disclosure. Other embodiments are contemplated within the scope of the present disclosure in addition to the exemplary embodiments shown and described herein. Modifications and substitutions by one of ordinary skill in the art are considered to be within the scope of the present disclosure.

What is claimed:

1. A thoracic lumbar sacral orthosis back brace, comprising:
   a lumbar portion, comprising:
     a central portion; and
     a pair of belts, adjustably connected to the central portion;
   a thoracic portion, comprising:
     a central thoracic portion;
     a thoracic panel; and
     a pair of shoulder straps being connected at a first end of the thoracic panel;
   a bowtie portion of fixed length being fixedly attached to a central thoracic stabilizer to form a channel for slidably engaging with a second end of the thoracic panel, further comprising a stay with a serpentine configuration embedded within the bowtie portion that extends at least a portion of a total horizontal length of the bowtie portion that provides additional rigidity to the bowtie portion; and
   a pair of adjustment straps forming a three point adjustment system such that a first pair of adjustment points is located at free ends of the pair of shoulder straps, a second pair of adjustment points is located at each of a pair of fixed loops attached to respective end regions of the bowtie portion, and a third pair of adjustment points comprise a pair of connection points each located on one of the adjustable belts.

2. The thoracic lumbar sacral orthosis back brace of claim 1, wherein the bowtie portion is oriented parallel to the lumbar portion.

3. The thoracic lumbar sacral orthosis back brace of claim 1, wherein the bowtie portion has a length that is approximately equal to a width of the central portion.

4. The thoracic lumbar sacral orthosis back brace of claim 1, wherein a spacing of the second pair of attachment points is adjustable.

5. The thoracic lumbar sacral orthosis back brace of claim 1, wherein the first pair of adjustment points, the second pair of adjustment points, and the third pair of adjustment points are disposed on an exterior surface of the thoracic lumbar sacral orthosis back brace.

6. The thoracic lumbar sacral orthosis back brace of claim 1, wherein the first pair of adjustment points, the second pair of adjustment points, and the third pair of adjustment points are each adjustable with respect to the pair of adjustment straps.

7. The thoracic lumbar sacral orthosis back brace of claim 1, further comprising a stabilizer embedded within the thoracic panel.

8. The thoracic lumbar sacral orthosis back brace of claim 7, wherein the stabilizer is comprised of a high density polyethylene (HDPE) sheet or a laminated HDPE.

9. The thoracic lumbar sacral orthosis back brace of claim 7, further comprising a pair of arm strap stabilizers configured to stabilize the pair of shoulder straps.

10. The thoracic lumbar sacral orthosis back brace of claim 1, wherein the thoracic lumbar sacral orthosis back brace is comprised of a plurality of layers, including an innermost layer, a first intermediate layer, a second intermediate layer, and an outer layer that comprises an upper portion of a back panel.

11. The thoracic lumbar sacral orthosis back brace of claim 10, wherein the innermost layer comprises a phase change material (PCM), the first intermediate layer comprises a foam layer, the second intermediate layer comprises a plastic material, and wherein the upper portion of the back panel is a heat moldable plastic or cross-linked polyurethane foam pad applied to the plastic material of the second intermediate layer.

* * * * *